US005741807A

United States Patent [19]
Thomas

[11] Patent Number: 5,741,807
[45] Date of Patent: Apr. 21, 1998

[54] HISTIDINE COMPOSITIONS AND METHODS FOR TREATING OR PREVENTING INFECTIOUS AND NON-INFECTIOUS DIARRHEAS

[75] Inventor: Peter G. Thomas, Charlottesville, Va.

[73] Assignee: Cytos Pharmaceuticals, L.P., Durham, N.C.

[21] Appl. No.: 718,705

[22] Filed: Sep. 27, 1996

[51] Int. Cl.$^6$ ............................................. A61K 31/415
[52] U.S. Cl. ...................... 514/399; 548/339.1; 514/400
[58] Field of Search ............................ 514/400, 399; 548/339.1

[56] References Cited

U.S. PATENT DOCUMENTS

| | | | |
|---|---|---|---|
| 3,746,700 | 7/1973 | Parisi et al. | 514/400 X |
| 3,988,466 | 10/1976 | Takagi et al. | 514/400 X |
| 3,995,051 | 11/1976 | Cook et al. | 514/400 X |
| 4,332,814 | 6/1982 | Newsome et al. | 514/400 X |
| 4,339,378 | 7/1982 | Masaki et al. | 514/400 X |
| 4,342,774 | 8/1982 | Okabe et al. | 514/400 X |
| 4,508,728 | 4/1985 | Nagai et al. | 514/400 X |
| 4,612,324 | 9/1986 | Cashin et al. | 514/400 |
| 4,734,276 | 3/1988 | Ziegler | 514/400 X |
| 4,863,900 | 9/1989 | Pollock et al. | 514/400 X |
| 5,030,645 | 7/1991 | Kollonitsch | 514/400 X |
| 5,238,931 | 8/1993 | Yoshikawa et al. | 514/400 X |
| 5,280,038 | 1/1994 | Kukreja et al. | 514/400 X |

FOREIGN PATENT DOCUMENTS

| | | | |
|---|---|---|---|
| 008658 | 3/1980 | European Pat. Off. | 514/400 |
| 0 466 029 B1 | 1/1992 | European Pat. Off. | |
| 2289168 | 5/1976 | France | 514/400 |

OTHER PUBLICATIONS

Shenkar et al., "Effects of treatment with the 21-aminosteroid, U74389F, on pulmonary cytokine expression following hemorrhage and resuscitation." Critical Care Medicine 23(1):132–139 (1995).

Grimble, "Malnutrition and the immune response 2. Impact of nutrients on cytokine biology in infection." Transactions of the Royal Society of Tropical Medicine and Hygiene 88:615–619 (1994).

Grimble, "Nutritional Antioxidants and the Modulation of Inflammation: Theory and Practice," New Horizons 2(2):175–185 (1994).

Kelly et al., "Dimethyl Sulfoxide Modulates NF–κB and Cytokine Activation in Lipopolysaccharide–Treated Murine Macrophages." Infect. Immun. 62(8):3122–3128 (1994).

Simpson et al., "Acute Fulminant Stage Adult T-Cell Leukemia/Lymphoma in Rabbits Inoculated with an HTLV-1 Transformed Rabbit Cell Line," Journal of Acquired Immune Deficiency Syndrome 6(6):741 (1993).

Eugui et al., "Some antioxidants inhibit, in a co-ordinate fashion, the production of tumor necrosis factor–α, IL–β, and IL–6 by human peripheral blood mononuclear cells," Int'l Immunol. 6(3):409–422 (1993).

Bone, "Inhibitors of complement and neutrophils: A critical evaluation of their role in the treatment of sepsis," Critical Care Medicine 20(6):891–898 (1992).

Erickson et al., "Influence of Histidine on Lipid Peroxidation in Sarcoplasmic Reticulum," Archives of Biochemistry and Biophysics 292(2):427–432 (1992).

Fujimoto et al., "Histamine and histidine decarboxylase are correlated with mucosal repair in rat small intestine after ischemia–reperfusion," abstract, J. Clin. Invest. 89(1):126–133 (1992).

Maldonado et al., "Specific Serum Amino–acid Profiles of Trauma and Septic Children," Clin. Nutr. 7(3):165–170 (1988).

Gebhard et al., "Bretschneider's Histidine–Buffered Cardioplegic Solution: Concept, Application, and Efficiency," Myocardial Protection in Cardiac Surgery, pp. 95–119 (1987).

Harvey et al., "Dietary $_L$–Histidine–Induced Hypercholesterolemia and Hypocupremia in the Rat$^{1,2}$," J. Nutri. 111(4):639–647 (1981).

Spector et al., "Stimulation of mucosal growth by gastric and ileal infusion of single amino acids in parenterally nourished rats," abstract, Digestion 21(1):33–40 (1981).

Askanazi et al., "Muscle and Plasma Amino Acids Following Injury," Annl. Surg. 192(1):78–85 (1980).

Ferrante et al., "Optimal Conditions for Simultaneous Purification of Mononuclear and Polymorphonuclear Leucocytes from Human Blood by the Hypaque–Ficoll Method," J. Immunol. Meth. 36:109–117 (1980).

Schlech et al., 1985, JAMA, 253:1749–54.

Tunkel et al., 1980, Annals of Int. Med. 112:610–623.

Ferrante et al.; J Immulol. Meth. 36:109–117, 1990.

Cheson et al., 1976, J. Clin. Invest. 58:789–796.

Allen et al., 1976. Biochem. Bosphys. Res. Comm. 69:245–252.

Chang et al., 1987, Journal of Clinical Investigation 79:1498–1509.

Horgan, et al., 1990, American Journal of Physiology 259:L315–L319.

(List continued on next page.)

Primary Examiner—Floyd D. Higel
Attorney, Agent, or Firm—Iassc A. Angres; Susan P. Petraglia

[57] ABSTRACT

A method of preventing or reducing fluid and electrolyte losses in mammalian subjects under the effect of a stimulus that directly or indirectly causes such losses, by administering a therapeutically effective amount of D-histidine, L-histidine, a racemic mixture thereof, a non-racemic mixture thereof, and pharmaceutically acceptable salts in conjunction with a carrier. In one embodiment the method is useful in reducing or preventing intestinal tract fluid secretions, and fluid and electrolyte losses associated with diarrhea arising from a number of causative agents, such as infectious diarrheas and non-infectious diarrheas. Various therapeutic regimes of histidine administration and formulation are embodied. Therapeutic compositions of histidine in combination with other medicaments, e.g., those that produce a diarrheal side-effect, are disclosed as another embodiment.

34 Claims, 6 Drawing Sheets

OTHER PUBLICATIONS

McMurtry et al., 1976, Circulation Research 38:99–104.

Brashers, et al., 1988, Journal of Clinical Investigation 82:1495–1502.

Dawson, et al.; "Pulmonary microcirculatory hemodynamics"; Annals of the New York Academy of Sciences 384:90–116, 1982.

Sawasdikol et al.; "Infection of the Laboratory Rabbit with HIV-1 and HTLV-1"; AIDS Research Reviews, 2:211–233, 1992.

Kindt et al.; "Acute Mononuclear Cell Leukemia in Outbred Rabbits Inoculated with HTLV-I Transformed Rabbit Lines"; Int'l Cong. Immun., Aug., 1992.

Sawasdikol et al.; "Acute Mononuclear Cell Leukemia in Outbred Rabbits Inoculated with HTLV-I Transformed Rabbit Cell Lines"; FASEB J., Part II, vol. 6, No. 5, Apr. 5–9, 1992.

R. Berkow; The Merck Manual of Diagnosis and Therapy, 1982; pp. 54–57.

Quagliarello et al.; "Morphologic Alterations of the Blood-Brain Barrier with Experimental Meningitis in the Rat"; J. Clin. Invest. 77:1084–1095, 1986.

Wispelwey et al., "Haemophilus influenzel Lipopolysaccharide-induced Blood Brain Barrier . . . in the Rat"; J. Clin. Invest. 82:1339–1346; 1988.

Quagliarello et al.; "Bacterial Meningitis: Pathogenesis, Pathophysiology, and Progress"; New England Journal of Medicine, Sep. 17, 1992, pp. 864–872.

Kindt et al.; Acute Mononuclear Cell Leukemia in Outbread Rabbits Inoculated with HTLV-I Transformed Rabbit Lines; Int'l. Congress of Immunology, Aug. 1992(Abst).

Powell et al; "Effect of Oxygen–Free Radical Scavengers on Survival in Sepsis" The Amer. Surgeon 57(2) Feb. 1991, pp. 86–88.

Baruchel et al.; "The role of oxidative stress in disease progression in individuals ifected by the human immunodeficiency virus"; Journal of Leukocyte Biology, vol. 52, Jul. 1992, pp. 111–114.

Chang et al.; "Beneficial effect of a platelet–activating factor antagonist, WEB 2086, on endotoxin–induced lung injury"; 1990, American Physiological Society, pp. H153–H158.

HISTIDINE COMPOSITIONS AND METHODS FOR TREATING OR PREVENTING INFECTIOUS AND NON-INFECTIOUS DIARRHEAS

FIELD OF THE INVENTION

The invention relates to a novel method of preventing or reducing intestinal tract fluid secretions and losses of fluids and electrolytes in a mammalian subject by administering thereto an effective dosage of an enantiomer of histidine or a mixture of histidine enantiomers and pharmaceutically acceptable salts thereof. The invention is useful in treating a mammalian subject experiencing any disorder or an isolated adverse stimulus that causes fluid and electrolyte losses and/or an increase in fluid lo secretions from the intestinal tract. An effective method of treating diarrhea, both infectious and non-infectious types, is provided, as well as compositions of matter for carrying out the method.

BACKGROUND OF THE PRESENT INVENTION

Diarrheal diseases in humans and non-human animals are caused by a plurality of etiological factors, such as viruses, bacteria, parasites, and rotaviruses. The most prevalent are the gram-negative bacteria *Escherichia coli* (hereafter *E. Coli*) and *Vibrio cholerea*. Diarrhea resulting from these etiologic bases is termed "infectious." Diarrhea of the non-infectious type can result from drug therapy, diet, ulcerative colitis, Crohn's disease, diseased or partially impaired body organs such as the liver and immune system, and can also be a symptom of afflictions having an unclear etiologic basis (e.g., psychological stress.)

Diarrheal diseases are a prevalent cause of morbidity and mortality in less developed countries, killing an estimated 5 million persons per year, with newborn and young children being the most susceptible victims. For example, ten thousand people have died of cholera in Latin America since its outbreak in Peru in 1991. These diseases are not mutually exclusive to developing countries, but also afflict populations in developed countries. For example, each year in the US over 200,000 children 5 years and younger are hospitalized with acute diarrheal diseases. The infectious diarrheas are the leading cause of morbidity and mortality worldwide and the second or third most common class of illnesses in the United States after cardiovascular disease and respiratory infections.

Due to its many causes, acute infectious diarrhea can occur more than once in the same person, and, therefore, it is unlike most chronic conditions which typically occur once. For example, while most infectious diarrheas are acute with symptoms lasting from two to five days, certain infections, such as giardiasis, campylobacter, and amebiasis, may recur if the organisms are not erradicated. With some bacteria (e.g., Salmonella) it is possible that the subject is in a carrier state without symptoms. (Jinich H. Acute diarrhea. In Hurst J W, ed. Medicine for the practicing physician, 2nd ed. Boston 1988). Unlike other digestive diseases, infectious diarrheas are communicable via person-to-person contact or through contaminated food or water and can spread endemically or in epidemics through households, schools, day-care centers, nursing homes, and communities.

Diarrheal diseases also pose a serious challenge in the raising of non-human animals in the farming industry, particularly with young calves and pigs. The prevalent causes are infectious in origin. Rota and corona virus, a contagious intestinal infection, is common in calves and is characterized by calves born with a diminished capacity to produce lactase, an enzyme essential for the decomposition of milk. Consequently, diarrhea develops quickly in the young animals due to the osmotic effect in the intestinal tract. Swine dysentery in pigs is caused by *Treponema hyodysenteriae* and is characterized by mucohemorrhagic diarrheal stools. This infection impairs the growth of the pig and decreases the rate of food conversion. In addition, stresses on the young animals at the time of weaning, as a result of a change in fodder, maternal separation, and physical transportation, are a cause of non-infectious diarrhea.

Whether human or non-human animal, the life-threatening nature of diarrheal conditions is the result of dehydration and the acidosis that results. In the case of certain infectious diarrheas, it is believed that following oral ingestion, the bacteria adheres to the epithelial cells of the mucous membrane of the small intestine. There the bacteria reproduce (i.e., colonize), producing toxins which cause liquid to migrate from the mucous membrane to the lumen of the small intestine. This type of mechanism is known as noninflammatory (also known as secretory), and produces a watery diarrhea either directly or via elaboration of a true enterotoxin. For example, the toxins of certain gram-negative bacteria potentiate the activity of enzymes and intermediates (e.g., cyclic adenosine-5'-monophosphate) within the epithelial cells, causing a hypersecretion of fluid from the mucous membrane into the lumen. Cholera, giardiasis, and viral diarrheas are examples of this type of diarrheal mechanism.

Other mechanisms of infectious diarrhea are inflammatory and penetrating. Inflammatory, also known as invasive, occurs when organisms invade the gut mucosa (usually distal small bowel or colon) and produce a bloody diarrhea and systemic signs (e.g., fever). Salmonellosis, shigellosis, campylobacteriosis, and amebiasis are examples. Penetrating, also known as systemic infection, occurs when organisms penetrate the gut mucosa without disruption or extensive destruction and cause infection of multiple organs that is sometimes accompanied by diarrhea. Typhoid fever and Hepatitis A are examples.

To date, efforts to manage diarrheal diseases in afflicted subjects are aimed at rehydration therapies and anti-diarrheal medicaments. Rehydration therapy, which is oftentimes the most important aspect of treatment, typically comprises compositions of various salts and glucose, to quickly replenish lost water and ions and neutralize the acidosis that results from the loss of water and ions. Unfortunately, rehydration therapy does not stop the diarrheal occurrence.

Anti-diarrheal medicaments are well known in the medical field, are available in various forms, and act at different systemic and cellular levels of the afflicted host. These include systematically acting drugs, combinations of anti-cholinergics with spasmolytics, anti-bacterials and antibiotics, membrane receptor-specific medicaments that modulate receptor-dependent mechanisms, e.g., certain alpha2 adrenergic agonists, somatostatin, or enkephalin and morphine analogs, and vaccines. However, certain of these medicaments for the treatment of diarrheal diseases have side-effects and/or efficacy duration that makes them less desirable from a therapeutic standpoint. For example, long-term antibiotic therapy does not afford an acceptably high level of protection and disease management in areas with diarrheal epidemics. Clonidine, an alpha2 adrenergic agonist which is effective as an anti-diarrheal is reported to have anti-hypertensive effects. In the case where diarrhea is

3 caused by cholera toxin, the only protection is an inoculum of marginal efficacy and low duration of protection (3 months).

It is an object of the present invention to provide a novel method for the prophylaxis or, alternatively, treatment of intestinal tract fluid secretion and fluid electrolyte losses associated with dehydration caused by any causative agent that produces these symptoms.

It is a further object of the invention to provide a novel prophylaxis or treatment of the above-mentioned fluid secretions and electrolyte losses associated with diarrheal episodes.

It is yet a further object of the invention to provide novel compositions of matter useful in the practice of method according to the invention.

SUMMARY OF THE INVENTION

The foregoing and other objects are realized, and some of the disadvantages and drawbacks of prior art therapies avoided, by administering a therapeutic dosage of histidine, in conjunction with a pharmaceutically acceptable carrier, to a mammalian subject experiencing any one of intestinal tract fluid secretions, and fluid and electrolyte loss.

More particularly, the present invention embodies administering to a mammalian subject having an affliction, or prone to an affliction that is characterized by increased intestinal tract fluid secretions and/or fluid and electrolyte losses, a composition containing a therapeutically effective dose of either D-histidine, L-histidine, mixtures thereof (both racemic and non-racemic), or pharmaceutically acceptable salts of any of the foregoing, to prevent or reduce these secretions and/or fluid and electrolyte losses in the afflicted subject. Histidine has the following chemical structure:

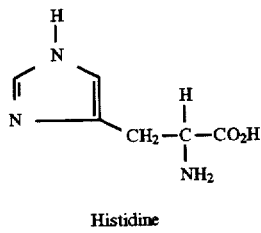

Histidine

BRIEF DESCRIPTION OF THE FIGURES

The file of this patent contains at least one drawing executed in color. Copies of this patent with color drawings will be provided by the Patent and Trademark Office upon request and payment of the necessary fee.

The following figures constitute a part of this specification and are incorporated to further exemplify the embodiments of the invention and, particularly, to demonstrate the utility thereof.

DETAILED DESCRIPTION OF THE INVENTION

Figure 1:
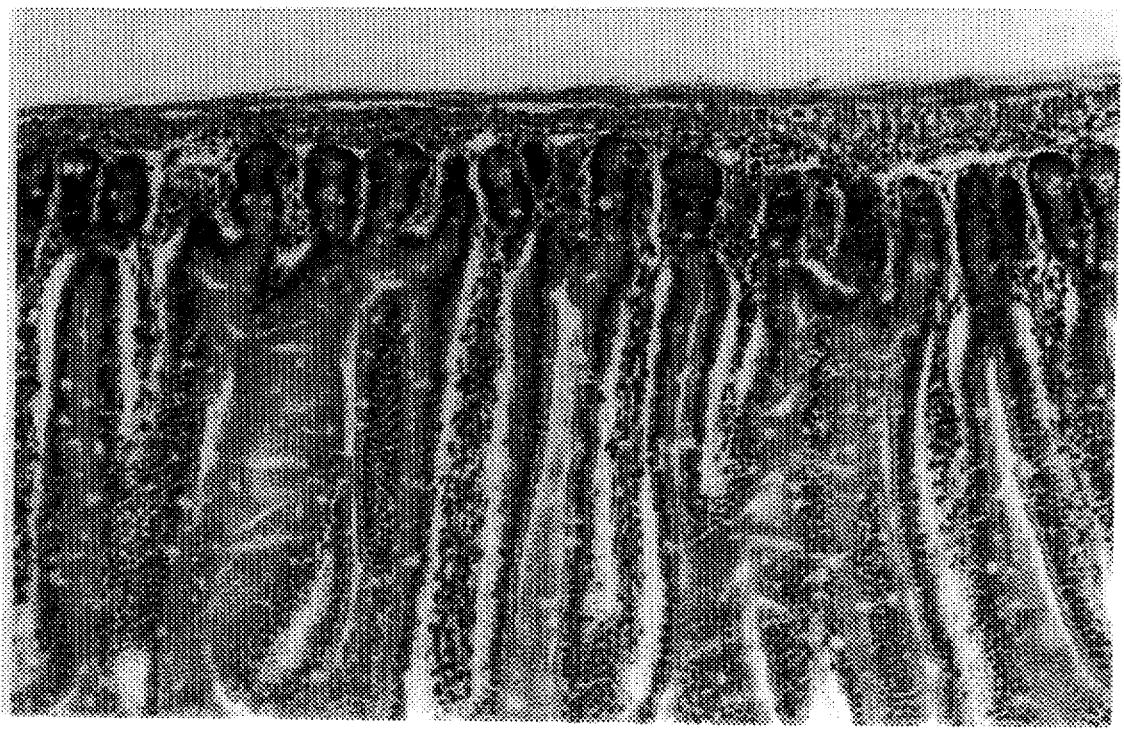
FIG. 1 illustrates a fixed and stained murine intestinal tissue sample from Example 1, under light microscopy at 160 X, of a PBS-treated control tissue after 8 hrs.

The prophylaxis and treatment that are one aspect of the invention are effective either to prevent the onset or reduce the existence of the afore-noted intestinal tract fluid secretions and/or losses of fluids and electrolytes regardless of the causative agent producing these symptoms. The symptoms treatable or prevented by administration of the histidine compositions of the invention are those arising from a number of adverse stimuli or causative agents. A most common manifestation of intestinal tract fluid secretions and loss of fluid and electrolytes is with diarrheal conditions. The therapeutic histidine compositions and methods herein are effective as anti-diarrheals, regardless of the cause of the diarrheal episode. Hence, the diarrhea is itself a symptom of the underlying etiologic basis.

The cellular secretions and fluid/electrolyte losses of diarrhea that are prevented or treated by the present discovery may have any one of the following underlying causes: Infectious diarrhea arising from bacteria, viruses, retroviruses, parasites, fungi, protozoa, and toxins produced thereby; preferably, diarrhea arising from Salmonella, Shigella, V. cholera, Campylobacter, Clostridium difficile, E. Coli, rota viruses, corona viruses, Trepomena hyodysenteriae, and toxins produced thereby. It is also within the purview of the invention to treat or prevent cellular secretions and fluid/electrolyte losses associated with diarrhea arising from any genetic variants of the above agents, whether naturally or artificially produced. Most preferably, the methodology herein is useful in preventing or treating diarrhea arising from Salmonella and V. cholera (both cholera toxin-producing strains and strains that do not produce cholera toxin), and genetic variants thereof. Although cholera toxin is the critical diarrheogenic factor in cholera, strains of V. cholera that do not produce cholera toxin may also cause diarrheal illness, albeit to a milder extent than that caused by the toxin. A non-limiting example is a non- cholera toxin-producing strain of V. cholera that produces a heat-stable enterotoxin (NAG-ST) that is almost identical to the STa heat-stable enterotoxin of E. coli. See, Morris, J. G., "Cholera And Other Vibrioses" in INFECTIOUS DISEASES, A Treatise of Infectious Processes, 5th Edition, Hoeprich, P. D. et al, Chapter 80 (1994). Other non-cholera toxin-producing strain of V. cholera that may cause diarrheal illness are known to those having ordinary skill in the art and are within the methodology of the invention.

The compositions and methods of the invention are useful in treating or preventing the following instances of diarrhea arising as a side-effect of anticancer agent or radiation therapy, or a combination thereof. Diarrhea arising from an inflammatory bowel disease in general, and, more particularly, ulcerative colitis, Crohn's disease, and irritable bowel syndromes. Diarrhea arising from a bodily intolerance of an ingested food item, in general, and, preferably diarrhea arising from an enzyme deficiency and malabsorption conditions. Most preferably, diarrhea arising from a deficiency of a lactose-decomposing enzyme (i.e., a lactase.)

It is also intended that diarrhea arising from any combination of two or more of the above exemplified causative agents can be prevented or reduced using the inventive histidine compositions. Although not wishing to be bound by a particular theory, it is thought that the effectiveness of histidine mixtures, or of either enantiomer alone, in preventing or reducing intestinal tract fluid secretions and/or fluid/electrolyte loss is due to the inactivation of $PGE_2$ prostaglandins.

Diarrheal episodes that are prevented or treated with the instant histidine compositions also include those that arise as a side effect of a medicament other than a cancer chemotherapeutic agent. By way of example, antibiotics (e.g., penicillins, aminopenicillins, amoxicillin, erythromycin, cephalosporins such as cefuroxime axetil, fluoroquinolones such as ciprofloxacin, enoxacin, lomefloxacin, norflox, and ofloxacin; and chloramphenicol), antifungal/antibiotics (e.g., nystatin), interferon beta-1b (rIFN-B), interferon gamma, toxoids such as diptheria and tetanus toxoids and whole-cell Petussis and Haemophilus influenzae Type B conjugate vaccines, varicella virus vaccine, hepatitis A vaccine (inactivated) and hepatitis B vaccine, gastric antisecretory compounds/proton pump inhibitors (e.g., lansoprazole, omeprazole, and misprostol) histamine $H_2$ antagonists (e.g., cimetidine and famotidine), antiemetic/antivertigo anticholinergics (e.g., cyclizine and meclizine), other antiemetic/antivertigo agents (e.g., phosphorated carbohydrate solution with fructose, and granesitron HCl), antimigraine agents (e.g., sumatriptan succinate), anti-gout agents (e.g., cholchicine, allopurinol, and methotrexate), antirheumatic agents (e.g., hydroxychloroquine sulfate), antipsychotic agents (e.g., lithium, piniozide, and clozapine), antianxiety agents (e.g., benzodiazepines), antidepressants (e.g., paroxetine, and selective serotonin reuptake inhibitors such as fluoxetine, fluvoxamine, sertraline, venlafaxine, and bupropion HCl), nonsteroidal anti-inflammatory drugs (e.g., diciofenac, flurbiprofen, etodolac, ketoprofen, ketorolac, meclofenamate, and nabumetone), antihyperlipidemic agents (e.g., HMG-CoA reductase inhibitors such as fluvastatin, lovastatin, pravastatin, and simvastatin, and probucol), antihypertensive agents (e.g., losarian and ACE inhibitors), diuretic agents (e.g., thiazides, threloops diuretics, and potassium-sparing diuretics), cardiac glycoside agents (e.g., digitoxin, deslanoside, and digoxin), antianginal agents, antiarrhythmic agents, peripheral vasodilating agent, β-adrenergic blocking agents, and anorexiants. This list of therapeutic agents that can produce a diarrheal side effect is not intended to be limiting of the invention. It is within the intended scope of the invention that any medicament producing a diarrheal side effect (as reported, for example, in Drugs: Facts and Comparisons, 50$^{th}$ Edition (1996)) can have the fluid/electrolyte losses and hypersecretions associated therewith abated or prevented by administering a therapeutic dosage of histidine in accordance with the invention. It is also intended that diarrhea arising from a combination of multiple medicaments (e.g., those enumerated above) administered simultaneously to a mammalian subject can be prevented or reduced.

A diarrheal episode can also arise from an idiopathic condition, unrelated to any other underlying disease state. It is also within the scope of the invention to use the present histidine compositions to reduce or prevent extracellular fluid secretions, fluid/electrolyte losses, as well as provide intestinal tissue protection from the damaging effects associated with this type of diarrheal occurrence.

The active agent of the present invention, histidine, in either of its enantiomeric forms, racemate form, free base, and salt forms is readily commerically available from numerous chemical and pharmaceutical suppliers. Where it is useful in the practice of the invention to employ a mixture of D- and L- histidine that is enriched in one enantiomer, such a mixture can be prepared by physically admixing the desired quantity of each of the enantiomers.

The control of diarrheal symptoms achieved by the method of the present invention is obtained by administering a therapeutically effective dosage of a histidine as specified above, or a pharmaceutically acceptable salt thereof, in conjunction with a pharmaceutically acceptable carrier. The precise therapeutic dosage of histidine to be employed depends upon several factors, including the host, the nature and the severity of the condition being treated, and the mode of administration. The assessment of these factors is well within the skill of the treating physician or veterinarian, as well as the determination of the precise dosage. However, in general, satisfactory inhibition of symptoms or prevention of the onset thereof is achieved when histidine is administered at a daily dosage of between 1 and 2000 mg/kg of body weight, or for most larger primates, at a dosage of between 50 and 500 mg/kg. A preferred total daily dosage for most larger primates is between and 100 and 350 mg/kg. For human infants a preferred total daily dosage is from about 5 mg to about 250 mg/kg of body weight.

It is yet another embodiment of the invention to form and use compositions of histidine in conjunction with another active ingredient, such as another therapeutic agent that produces a diarrheal side-effect, such as the types listed above, or one that functions so that diarrhea does not result, for example, a lactose-decomposing enzyme. It is also contemplated that when combining a therapeutically effective amount of histidine with another medicament having an antidiarrheal effect, that a potentiated (i.e., more than additive) level of protection may be obtained.

In veterinary applications, for example in treating diarrheal outbreaks among adult and infant cows and swine, the dosage of histidine to be administered in accordance with the present invention can be selected in consideration of the animal's age, severity of infectious diarrhea, and the route of administration. In general, a total daily dosage of histidine of symptoms or prevention thereof is from about 1 g to 10.0 g/kg of body weight, preferably from about 2 g to 7.5 g/kg.

A histidine in accordance with the invention is formulated in conjunction with at least a pharmaceutically acceptable carrier. There are numerous and diverse types of acceptable carriers which are readily appreciated by those skilled in the art depending on the route of histidine administration. The routes of histidine administration that are appropriate in the practice of the invention include oral, rectal, intraintestinal, intramuscular, intraperitoneal, intranasal, intravenous (I.V.), implant and transdermal. Optimized efficacy of the methodology herein can be achieved in certain instances by combining two different routes of administration in a course of therapy. For example, I.V. administration followed by intraperitoneal administration, or intraintestinal administration followed by oral tablets or liquid formulation.

Formulations suitable for parenteral administration conveniently comprise sterile aqueous preparations of histidine which are preferably isotonic with the blood of the recipient.

Suitable such carrier solutions include phosphate buffered saline, saline, water, lactated ringers or dextrose (5% in water). Such formulations may be conveniently prepared by admixing histidine with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives (when the formulations are presented in multi-dose containers), buffers to provide a suitable pH value for the formulation, and sodium chloride, or glycerin, to render a formulation isotonic with the blood.

For I.V. administration, histidine may be used in free or salt form (for example, salts of alkali and alkaline earth metals such as sodium and calcium, respectively, salts if mineral acids such as HCl and sulfuric acid, or salts of organic acids, such as acetic acid. Amine addition salts may also be used in the practice of the invention, for example a phosphate amine addition salt. Examples of typical carriers are sterilized water, saline, and phosphate buffered saline. Optional additives include isotonic agents, stabilizers, pH controlling agents, agents necessary for the proper infusion of solutions, and water soluble nutrients.

Transdermal administration can be accomplished using preparations in the form of ointments, emulsions, lotions, solutions, creams or transdermal patches. Suitable pharmaceutical carriers for transdermal administration include, for example, polyethylene glycol, propylene glycol, isopropanol, ethanol, oleic acid, N-methylpyrrolidone, sesame oil, olive oil, wood alcohol ointments, vaseline, and paraffin, or mixtures thereof. When histidine is formulated in a transdermal patch, the therapeutic dose can be incorporated either directly in an adhesive layer that fixes a drug impermeable backing to the skin of the treated-subject, or can be incorporated in a matrix layer and released therefrom in controlled fashion. Suitable adhesive layer carriers for histidine include, for example, polyisobutenes, polyisobutylenes, polyacrylates, polyurethanes, polysiloxanes, polystyrene copolymers, EVA-copolymer, and polyether amide block copolymers. Suitable drug-releasing matrices include, for example, natural or synthetic rubbers, polymeric materials, such as EVA copolymers, thickened mineral oil, and petroleum jelly. Optional constituents for the transdermal administration of histidine include drug permeable rate-controlling membranes and penetration enhancers which are well known to those skilled in the transdermal formulation art.

Suppository administration is particularly well suited for patients with disorders in digestive organs and for infant patients, and affords constant release over an extended period of time. Typical base carrriers for suppoitories include, for example, natural, synthetic or partially synthetic fats, waxes and derivative thereof from animal, vegetable, or mineral origin. Specific examples inlcude olive oil, corn oil, castor oil, hydrogenated oils, petrolatum, solid paraffin, ligind paraffin, carnuba wax, bees wax, lanolin partially or totally synthetic esters of glycerol fatty acid, mono, di, or triglycerides of saturated or unsaturated fatty acids, and others well known in the art. Other additives suitable for incorporation into a suppository of the invention include preservative, stabilizers, surfactants, pigments, pH modifiers and purified water.

For intranasal administration of histidine, the choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives (e.g., antimicrobials), surfactants (e.g., non-ionics such as polysorbates) jelling agents, buffering and other stabilizing agents (e.g., antioxidants and metal chelating agents) and solubilizing agents (e.g., solubility enhancers) may also be present. Preferably, the nasal dosage form should be isotonic with nasal secretions. Although histidine can be formulated in water, more preferably it will be formulated in a solution buffered to a pH of between about 3.0 and 8.0, and most preferably pH 5.0–5.4 using e.g., a buffer system such as an acetate buffer, a phosphate buffer, a citrate buffer, and a succinate buffer.

For oral administration, histidine is formulated with a pharmaceutically acceptable solid or liquid carrier. Solid form preparations include powders, tablets, pills, capsules, cachets, and dispersible granules. A solid carrier can be one or more substances which may also act as diluents, flavoring agents, solubilizers, lubricants suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders, capsules and tablets preferably contain from five or ten to about seventy percent of the active compound. Suitable carriers are magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

Another type of solid carrier useful in the practice of the invention is a foodstuff. Solid foodstuffs suitable for admixture with a therapeutic dosage or unit dosage of histidine are, for example, cereals, chewing gum, crackers, candies, meats, vegetable and fruit preparations for babies, and cookies. For veterinary applications, histidine may be admixed directly into a grain ration of incorporated into a salt block. Likewise, histidine may be formulated with a liquid foodstuff, for example, milk, infant formula, juices, liquid vitamin supplements, and oral rehydration solutions.

Liquid form preparations include solutions, suspensions, emulsions, for example, of water aqueous solution, or other liquids, half-liquid bases, or optionally in pharmaceutically acceptable solvents (e.g., DMSO-propylene glycol solutions).

Also included are solid form preparations which are intended to be converted, shortly before use, to liquid for preparation for oral or rectal administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses contianing appropriate quantities of the active component. The unit dosage form can be a packaged preparation, the package containing discrete quantities of preparation, such as packeted tablets, capsules, lotions, ointments and powders in vials or ampoules. Also, the unit dosage form can be a capsule, tablet, cachet, or lozenge itself, or it can be the appropriate number of any of these in packaged form.

It is also within the scope of the invention to administer histidine in a time-release formulation such as a bolus for veterinary therapies. A wide variety of methods are now available in the art for preparing time-release or long-acting compositions. Any of these time-release or long-acting formulations are suitable in the practice of the present invention as long as it does not adversely affect the effectiveness of histidine in the treatment or prevention of extracellular fluid secretions and fluid/electrolyte losses. Advantages of time-release formulations include a lower concentration of peak serum absorption which substantially reduces any possible adverse side effects and/or toxicity of the active administered. In addition, a reduced frequency of administration results, which substantially improves patient compliance. A frequency of administration of every 12 to 24 hours would be preferred. In addition, a more constant concentration of histidine would result, and consequently, a more consistent relief or prophylaxis of symptoms.

DESCRIPTION OF THE PREFERRED EMBODIMENTS

Among the preferred embodiments are compositions of, and methods of using a therapeutically effective amount of histidine as defined above for the prevention or treatment of infectious diarrhea arising from Salmonella, and *V. cholera* toxin. Preferably the compositions are administered intraperitoneally, intraintestinally, or a combination thereof, to the subject in need of such prophylaxis or treatment.

Also, the compositons of the invention are effectively used to treat or prevent non-infectious diarrhea associated with ulcerative colitis, Crohn's disease, various irritable bowel syndromes, and idiopathic conditions. In addition to the ability of the histidine compositions to prevent or reduce intestinal tract fluid secretions and fluid and electrolyte losses, the compositions herein also afford protection to intestinal tissue that would otherwise be damaged by the diarrheal condition. Preferably the compositions are administered intraperitoneally, intraintestinally, or a combination thereof, to the subject in need of such prophylaxis or treatment.

Another preferred embodiment are compositons of a therapeutically effective amount of histidine as defined above in combination with a therapeutically effective amount of an antibiotic, especially one that causes pseudomembranous colitis. Since pseudomembranous colitis is caused by an overgrowth of intestinal flora *Clostridium difficile*, another preferred embodiment herein is a method of preventing or treating diarrhea arising from *Clostridium difficile* using the histidine compositions of the invention.

Still yet another preferred embodiment is a compositions of a therapeutically effective amount of histidine as defined above in combination with a therapeutically effective amount of a lactose-decomposing enzyme and a pharmaceutically acceptable carrier as a prophylactic preparation for both human and non-human animal lactose intolerant subjects.

Further still is a preferred method of preventing or treating post-antibiotic pseudomembranous colitis in a mammalian subject undergoing an antibiotic therapy, which comprises administering to a mammalian subject a therapeutically effective amount of at least one of D-histidine, L-histidine, a racemic mixture thereof, a non-racemic mixture thereof, and pharmaceutically acceptable salts thereof, and a pharmaceutically inert carrier, for a period of time which is at least concurrent with the course of antibiotics, and, most preferably extends beyond the antibiotic therapy.

Having now generally described the invention, the same will be better understood by reference to certain specific examples, which are included for purposes of illustration only and not to limit the invention, any embodiment thereof, or of the appended claims.

The following experiments and data demonstrate the ability of histidine to provide protection against intestinal fluid loss arising from luminal challenge with specific infectious agents.

EXAMPLE 1

Swiss-Webster outbred mice were housed under conventional conditions and fasted for 24 hr. before challenge. L-Histidine free base (WPLP-14) was formulated by dissolving the drug in pyrogen-free $H_2O$ to 3.8% and then adjusting to 300 millimoles with 1M NaCl. The drug solution was filter sterilized and stored at 4° C. before use. The bacterial cells were resuspended in the drug solution or PBS and adjusted to an optical density of 0.9 using 600 nm. This challenge dose corresponds to approximately $4 \times 10^9$ cfu of *Salmonella typhimurium* strain 14028. The mice were anesthetized with ether and a single segment was constructed in the small intestine by ligation with silk suture. The challenge volume per intestinal segment was 100 µl. Every 2 hr. post infection, the drug-treated mice received a 100 µl injection of the drug solution into the peritioneal cavity. After 8 hr., the mice were killed by cervical dislocation, and the amount of fluid was measured and expressed as the volume in µl per cm of intestinal loop. The length of each loop should be at least 5 cm; however, some variation is to be expected due to the smooth muscle contractility and approximation during surgery. For this reason, the fluid accumulation results are always expressed per length (cm) of small intestine. The results are set forth in Table 1.

To assess whether histidine might be either toxic or have antibiotic-like activity that would diminish the virulence of *S. typhimurium* 14028, a lawn of *S. typhimurium* was set up on Mueller-Hinton agar plates and applied thereto were filter disks that were saturated in the 3.8% histidine solution injected into the mice. After overnight incubation, no inhibition of bacterial growth was observed. This experiment confirmed that the drug did not exert any direct effect on the bacteria used for challenge.

TABLE 1

Protection of Swiss-Webster Mice against Intestinal Challenge with *Salmonella typhimurium* 14028 using WPLP-14

| Mouse Group | Individual Responses | Fluid Accumulation (µl/cm) X ± S.D. | P |
|---|---|---|---|
| Control | 200 | 160 ± 38 | |
| | 182 | | |
| | 167 | | |

TABLE 1-continued

Protection of Swiss-Webster Mice against Intestinal Challenge
with *Salmonella typhimurium* 14028 using WPLP-14

| Mouse Group | Individual Responses | Fluid Accumulation (µl/cm) X ± S.D. | P |
|---|---|---|---|
| WPLP-14 | 160<br>89<br>83<br>73<br>14<br>11<br>0 | 36 ± 35 | 0.0013360 |

The data indicate that the mice dosed with L-histidine (100 µl luminally at challenge, and 100 µl interperitoneally every 2 hours) had significantly less fluid accumulation per length of small intestine than the control group.

Also, small intestinal tissues from the control and histidine-dosed mice were collected, fixed in 10% buffered formalin, and embedded in paraffin. Sections of tissue were cut, deparaffinized, and stained with haematoxylin and eosin. The samples were examined by light microscopy to observe the protective effect of histidine against tissue damage and whether the influx of inflammatory cells is affected by drug administration. Photo reproductions of control, bacterially challenged, and challenged/histidine-administered tissue samples, as viewed under 160X and 400X magnification, are depicted in FIGS. 1–6.

FIG. 1 (PBS Control @8 hrs (no challenge, no drug); 160X) represents a section showing normal small intestinal tissue 8 hours after injection with phosphate buffer solution. Villi and crypts are typical with epithelium intact, and goblet cells containing mucus are clearly visible along the epithelial surface.

Figure 2:
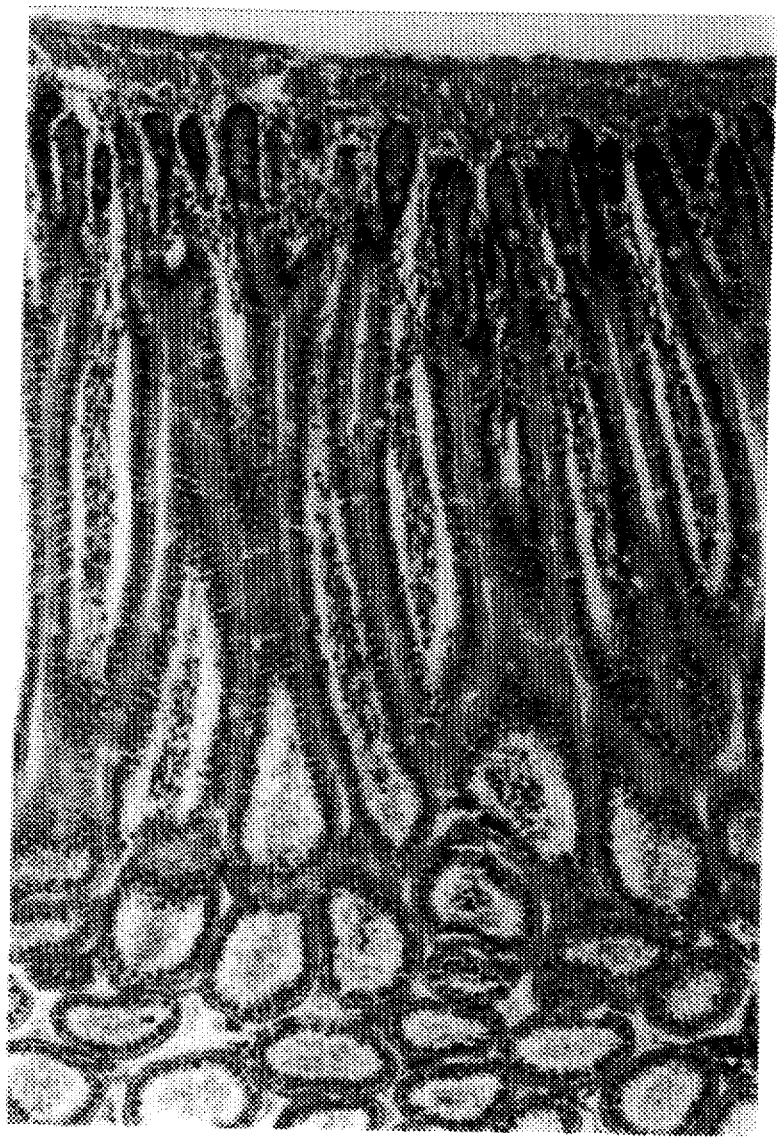
FIG. 2 illustrates a fixed and stained murine intestinal tissue sample from Example 1, under light microscopy at 160 X, of a histidine-treated control tissue after 8 hrs.

FIG. 2 (Histidine Control @8 hrs (no challenge); 160X) represents a section of small intestinal tissue that has been exposed to histidine only. The histological appearance of this section is indistinguishable from that of the PBS control shown in FIG. 1. Therefore, the drug exerts no detectable alterations in tissue morphology after 8 hours exposure in the intestinal lumen.

Figure 3:
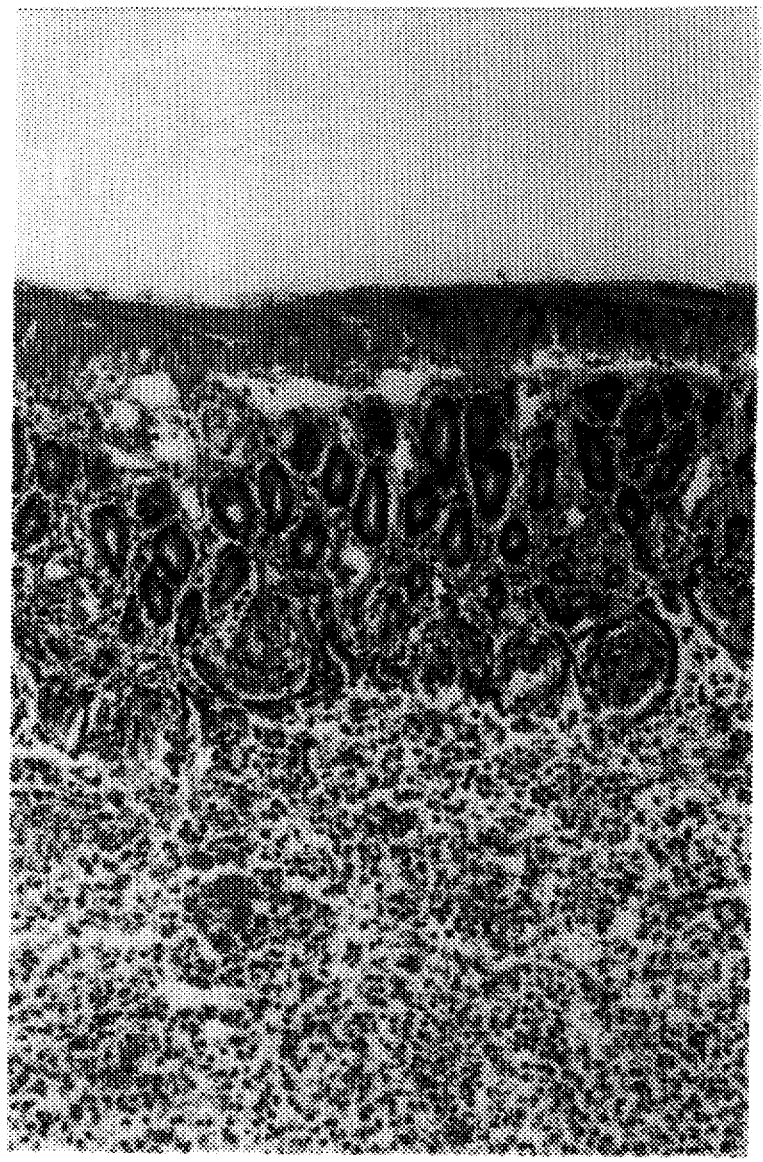
FIG. 3 illustrates a fixed and stained murine intestinal tissue sample from Example 1, under light microscopy at 160 X, of intestinal tissue after 8 hr. challenge with Salomnella typhymurium.

FIG. 3 (Salmonella challenge @8 hrs; 160X) shows tissue section with extensive damage to the small intestinal architecture due to acute inflammation and bacterial infection. The villi are completely destroyed and various types of intestinal cells are apparent in the intestinal lumen. Many of these free cells which have become dissociated from the small intestinal tissue are epithelial cells and others are polymorphonuclear neutrophils.

Figure 4:
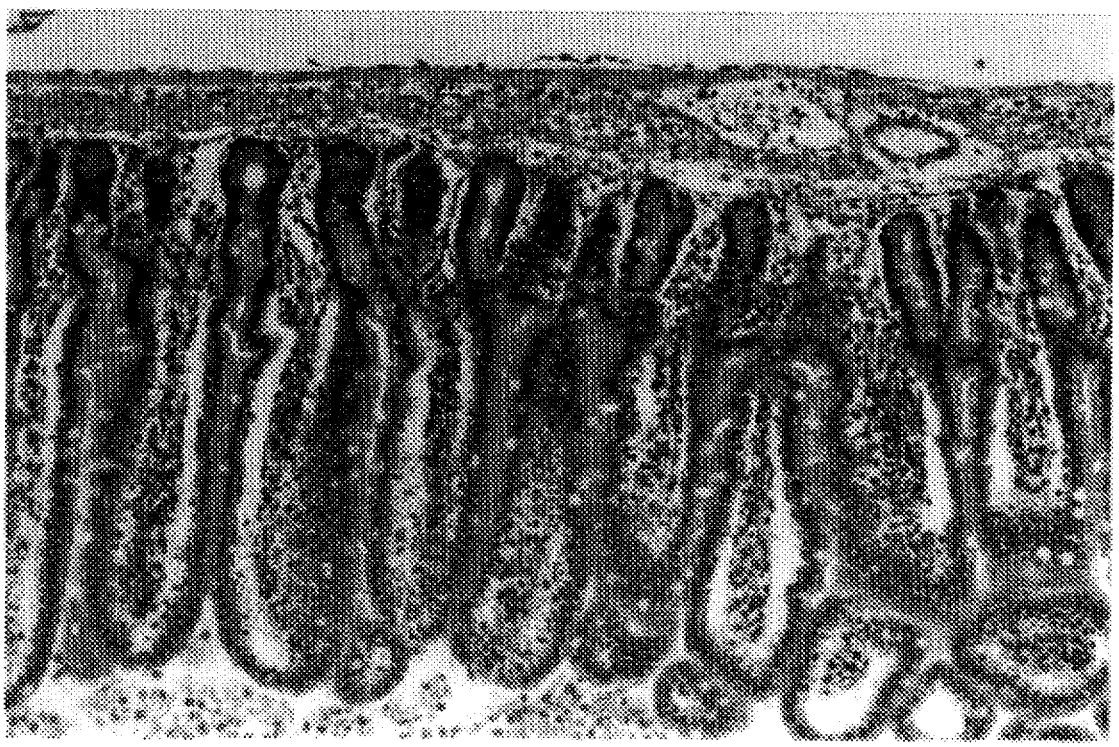
FIG. 4 illustrates a fixed and stained murine intestinal tissue sample from Example 1, under light microscopy at 160 X, of intestinal tissue after 8 hr. challenge with Salomnella typhymurium in conjunction with histidine administration.

FIG. 4 (Salmonella challenge+Histidine @8 hrs; 160X) shows that the tissue section has intact villi and crypts and goblet cells are present. At the tips of the villi, some cells are visible that have been released from damaged mucosa, however the amount of tissue damage in this area of the small intestine is minimal. Histidine has provided extensive protection from the damage caused by acute inflammation in response to the bacterial challenge.

Figure 5:
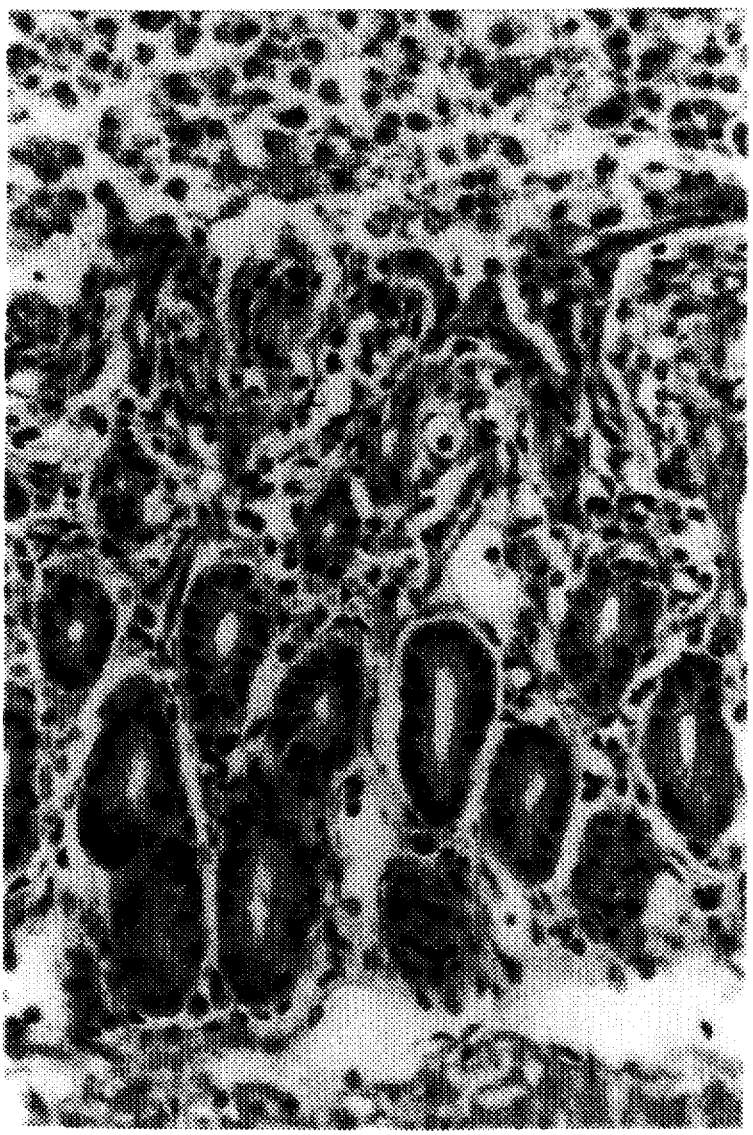
FIG. 5 illustrates a fixed and stained murine intestinal tissue sample from Example 1, under light microscopy at 400 X, of intestinal tissue after 8 hr. challenge with Salomnella typhymurium.

FIG. 5 (Salmonella challenge @8 hrs; 400X) confirms at higher magnification vis-à-vis FIG. 3 the morphological damage to the small intestinal mucosa caused by *S. typhimurium*. Examination of the cells released into the lumen revealed them to be many rounded epithelial cells as well as polymorphonuclear neutrophils. Also examination of the lamina propria indicated acute infiltration of inflammatory cells, for example, polymorphonuclear neutrophils.

Figure 6:
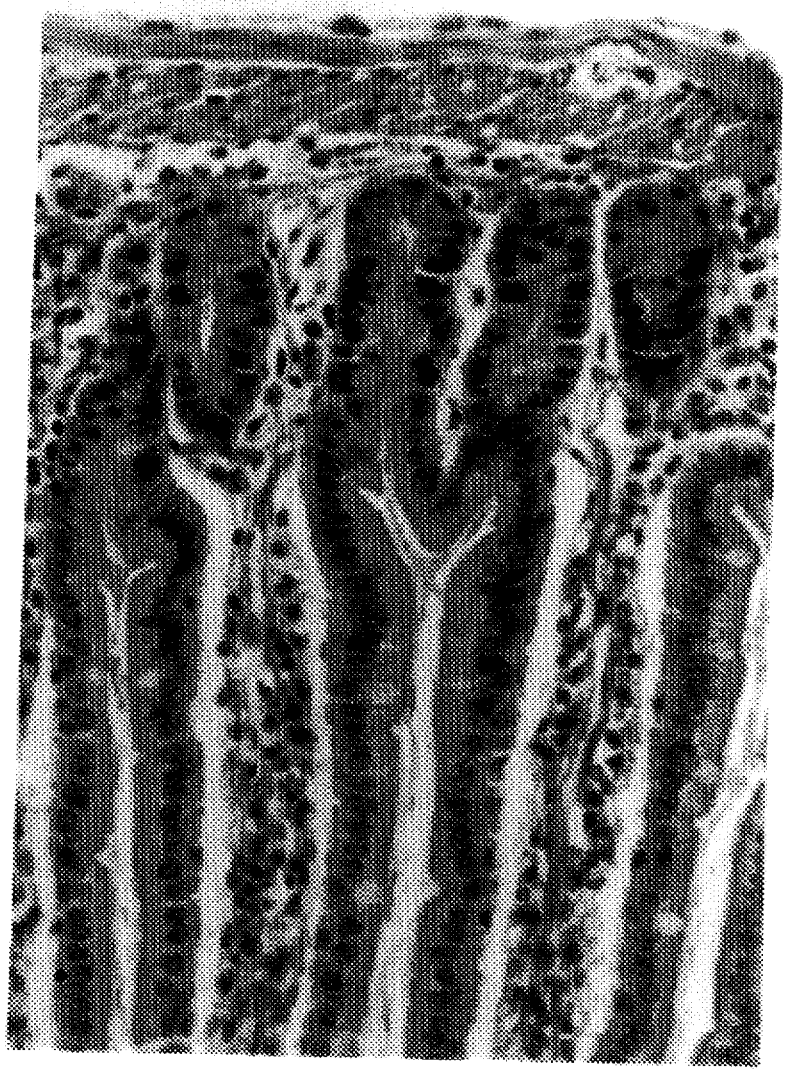
FIG. 6 illustrates a fixed and stained murine intestinal tissue sample from Example 1, under light microscopy at 400 X, of intestinal tissue after 8 hr. challenge with Salomnella typhymurium in conjunction with histidine administration.

FIG. 6 (Salmonella challenge+Histidine @8 hrs; 400X) reveals at higher magnification that the appearance of the histidine-treated small intestinal tissue is indistinguishable from that of normal tissue. Villi are lined with epithelial cells and goblet cells, and crypts appear normal. The overall appearance is that histidine has significantly reduced the damage due to acute inflammation.

EXAMPLE 2

The experimental procedure of Example 1 was repeated with the following modification.

Two groups of Swiss-Webster mice (8 mice per group) were challenged with *S. typhimurium* via the intestinal lumen. The single challenged dose of bacteria was resuspended in 100 µl of WPLP-14 (L-histidine free base, 3.8%) for the experimental group and injected into the small intestinal lumen. The control group challenge was suspended in PBS. Each mouse of group 2 received 200 µl of WPLP-14 in the peritoneal cavity at the time of surgery, as well as after 2 and 4 hours. The total time of bacterial challenge was reduced to 6 hours versus 8 hours in the previous example.

TABLE 2

Murine intestinal fluid accumulation responses (µl/cm) to *Salmonella typhimurium* WT comparing the effectiveness of WPLP-14 in protecting against fluid loss.
Fluid Accumulation (µl/cm)

| | | | | | | | | | |
|---|---|---|---|---|---|---|---|---|---|
| Group 1<br>S. typhimurium<br>WT (no drug) | 92 | 192 | 150 | 63 | 163 | 120 | 88 | 131 | 125 ± 43 |
| Group 2<br>S. typhimurium<br>WT + I.P. drug<br>(3 doses) every<br>2 hr | 77 | 35 | 33 | 0 | 57 | 0 | 50 | 0 | 32 ± 29<br>74%↓* |

*P = 0.0001732 by a two-tailed t-test; P = 0.0000866 by a one-tailed t-test
WT = wild-type strain 14028
↓ = decrease relative to control (no drug) group.
Each value represents a separate animal, and each group contained the intestinal fluid accumulation responses of eight mice.

From the results shown in Table 2, mice challenged with *S. typhimurium* and receiving WPLP-14(L-histidine free base) were protected against fluid loss (i.e., a 74% reduction in fluid accumulation) as compound to the control group.

EXAMPLE 3

The following experiments demonstrate the utility of histidine in reducing intestinal fluid accumulation initiated by intestinal challenge with cholera toxin ("CT"). In the experimental groups (Groups 2–6) mice in groups 2–5 were dosed intraperitoneally with WPLP-14 with the mice in group 6 receiving a single dose luminally at the time of challenge. Experimental groups 2–5 demonstrate the relative efficacies of various dosing patterns (i.e., multiple doses versus a single dose spaced a specified number of hours from initial challenge.)

In these experiments all mice received a cholera toxin challenge dose of 2 μg/loop and the mice in groups 2–6 received unit dosage of 100 μl of WPLP-14 (3.8%), whether singly or multiply dosed. The data are set forth in the following table.

TABLE 3

Murine intestinal fluid accumulation responses (μl/cm) to cholera toxin comparing the effectiveness of WPLP-14 in protecting against fluid loss.
Fluid Accumulation (μl/cm)

| | | | | | | | |
|---|---|---|---|---|---|---|---|
| Group 1 CT control (no drug) | 238 | 107 | 185 | 224 | 235 | 206 | 199 ± 45 |
| Group 2 CT + I.P. drug (3 doses) every 2 hr | 15 | 14 | 15 | 32 | 132 | 16 | 37 ± 43 |
| Group 3 CT + I.P. drug 0 time (1x) | 156 | 22 | 38 | 188 | 183 | 156 | 124 ± 68 38% ↓ |
| Group 4 CT + I.P. drug 2 hr delay (1x) | 18 | 213 | 186 | 125 | 160 | 13 | 119 ± 78 40% ↓ |
| Group 5 CT + I.P. drug 4 hr delay (1x) | 146 | 223 | 67 | 106 | 44 | 158 | 124 ± 60 38% ↓ |
| Group 6 CT + luminal drug 0 time (1x) | 163 | 69 | 0 | 107 | 95 | 42 | 79 ± 51 60% ↓ |

↓ = decrease relative to control (no drug) group.
Each value represents a separate animal, and each group contained the intestinal fluid accumulation responses of six mice.

EXAMPLE 4

The following experiment demonstrates murine intestinal fluid accumulation responses (μl/cm) to cholera toxin comparing the effectiveness of WPLP-14 (L-histidine) with D-histidine in protecting against fluid loss.

TABLE 4

Murine intestinal fluid accumulation response (μl/cm) to cholera toxin comparing the effectiveness of WPLP-14(L-histidine) with D-histidine in protecting against fluid loss.
Fluid Accumulation (μl/cm)

| | | | | | | |
|---|---|---|---|---|---|---|
| Group 1 CT control (1 μg) (no drug) | 171 | 210 | 190 | 220 | + | 198 ± 19 |
| Group 2 CT (μg) + I.P. | 19 | 0 | 167 | 152 | 0 | 68 ± 75 66% ↓* |

TABLE 4-continued

Murine intestinal fluid accumulation response (μl/cm) to cholera toxin comparing the effectiveness of WPLP-14(L-histidine) with D-histidine in protecting against fluid loss.
Fluid Accumulation (μl/cm)

| | | | | | | |
|---|---|---|---|---|---|---|
| D-histidine (3 doses) every 2 hr + luminal drug | | | | | | |
| Group 3 CT (μg) + I.P. WPLP-14 (3 doses) every 2 hr + luminal drug | 146 | 50 | 141 | 129 | 153 | 124 ± 358 37% ↓** |
| Group 4 S. typhimurium MudJ + oral drug ad libitum (2–3 days before challenge | 130 | 130 | 0 | 130 | 190 | 125 ± 66 18% ↓** |

+ Mouse died due to surgery
*P = 0.0296 by a two-tailed t-test; P = 0.0148 by a one-tailed t-test
**P = 0.016 by a two-tailed t-test; p = 0.008 by a one-tailed t-test
↓ = decrease relative to control (no drug) group.
Each value represents a separate animal, and each group contained the intestinal fluid accumulation responses of four–five mice.

EXAMPLE 5

The following formulations exemplify, but do not limit, various embodiments of the invention.

CAPSULE FORM

A) A capsule (22 mm length, 8 mm dia) was filled with a mixture that was prepared by combining 20 g of l-histidine free base with 60 g of lactose. One capsule contained 20 mg of the active substance.

B) Similarly, a capsule was prepared with a 100 mg dose of l-histidine free base by thoroughly admixing 100 mg dose of l-histidine with 100 g of lactose and filling a capsule of appropriate dimension.

TABLET FORM

A) 10 g of histidine were mixed with 60 g of lactose and 138 g of starch whereupon the mixture was wetted by a necessary amount of starch hydrogel. Two grams of magnesium stearate were added to the mixture after it was granulated and homogenized.

The mixture was then pressed to tablets. Each tablet was about 250 mg weight and 5 mm diameter and contained a 10 mg dose of the active substance.

B) Similarly, 500 mg tablets were prepared in which an amount of histidine corresponding to the 500 mg dose was added to proportionate amounts of lactose, starch hydrogel, and magnesium stearate, followed by granulating, homogenization, and pressing into tablets.

C) A tablet containing 250 mg of amoxicillin trihydrate and 200 mg of L-histidine was formulated with citric acid, corn starch, FD & C Red No. 40, flavoring, mannitol, magnesium stearate, saccharin sodium, silica gel and sucrose, in quantities routinely determined in the formualtion art.

SUPPOSITORY FORM 7.5 g of L-histidine was dispersed into purified water and 3 g of a fatty acid triglyceride was added to the dispersion.

After stirring to homogenize base was added in an amount to make the mixture pH 7.0, followed by the addition of purified water in an amount appropriate to make 100 g of a transparent gel with stirring. The gel was filled in 2.5 cc disposable syringes to obtain 50 pieces of syringed L-histidine injection preparation, each weighing 2 g and containing 150 mg of L-histidine.

I.V. SOLUTION

A) A typical i.v. solution for practice of the invention can be prepared by dissolving a specified number of moles of histidine to obtain the desired dose in sterilized water while stirring the solution to homogeneity. Acetic acid is added to the resulting aqueous solution of histidine to adjust the same to a pH of 7.0. The resulting aqueous solution is subjected to milipore filtration and charged under nitrogen gas into a vessel for an infusion solution. The product infusion solution was obtained by autoclaving under the usual conditions.

B) A combination therapy ready-for-use i.v. solution containing 0.2% ciprofloxacin and 10% L-histidine in a 5% dextrose solution, solubilized with lactic acid, and pH adjusted with HCl.

| SOLUTION FOR NASAL ADMINISTRATION | |
|---|---|
| D-histidine | 0.02–2 g |
| Sodium Acetate | 0.300 g |
| Methylparaben | 0.100 g |
| Propylparaben | 0.020 g |
| Sodium chloride | As needed for tonicity |
| Hydrochloric Acid or Sodium Hydroxide | To adjust pH |
| Purified Water | To 100 mL |

OINTMENT FOR TRANSDERMAL ADMINISTRATION

The following components are thoroughly admixed:

| A) | D/L histidine | 150 mg |
|---|---|---|
| | polyethylene glycol (avg. Mol. Wt. 1500) | 120 mg |
| | polyethylene glycol (avg. Mol. Wt. 400) | 240 mg |
| B) | D/L histidine | 50 mg |
| | vaselin | 710 mg |
| | paraffin liquid | 240 mg |

| TRANSDERMAL PATCH FORMULATION | |
|---|---|
| histidine HCl salt | 1–20% |
| vaselin | 20% |
| paraffin | 5% |
| polysiloxane adhesive | 55% |

Histidine hydrochloride salt is added under thorough mixing to a mixture of vaselin and paraffin (mixture I). The silastic elastomer is weighed directly to a tared mould to which mixture I is added and mixed thoroughly before adding a curing agent. The formulation is allowed to cure for 48 hours at room temperature and protected from light.

HISTIDINE/LACTASE COMBINATION FORMULATION

A) The following preparation is suitable for veterinary applications, e.g., young lactose intolerant calves having rota and corona virus infection. L-histidine HCl salt (2–3 g.) is admixed with lactase (up to 5% by weight of the overall composition), wheat bran as a filler, and with electrolytes (such as sodium chloride, potassium chloride, sodium citrate, citric acid, magnesium oxide, sodium hydrogen carbonate, and glucose), the exact quantities and proportions of filler and electrolyte composition being routinely calculated by standard veterinary practice. The above composition can be added to drinking water or to milk.

The following preparation is suitable for a lactose-intolerant human infant. D-histidine free base (30 mg.) and lactase in an infant-therapeutically-effective amount are added to a pureed baby food, such as vegetables or fruit, and administered prior to giving the infant a bottle of milk. Alternatively, the histidine and lactase can be added directly to the infant's milk.

The invention now being fully described, it will be apparent to one of ordinary skill in the art that many changes and modifications can be made thereto without departing from the spirit or scope of the invention as set forth herein. It is therefore to be understood that within the scope of the appended claims, the invention may be practiced otherwise than as specifically described herein.

What is claimed is:

1. A method of preventing or reducing at least one of intestinal tract fluid secretions, fluid loss, or electrolyte loss in a mammal, wherein said at least one of extracellular fluid secretion, fluid loss, or electrolyte loss is a result of an adverse stimulus on said mammal, by administering to said mammal a therapeutically effective amount of at least one of D-histidine, L-histidine, a racemic mixture thereof, a non-racemic mixture thereof, or pharmaceutically acceptable salts thereof.

2. A method of preventing or reducing at least one of intestinal tract fluid secretions, fluid loss, or electrolyte loss in a mammal having diarrhea, by administering to said mammal an effective amount of at least one of D-histidine, L-histidine, a racemic mixture thereof, a non-racemic mixture thereof, or pharmaceutically acceptable salts thereof.

3. The method according to claim 2 wherein the diarrhea is an infectious diarrhea.

4. The method according to claim 3 wherein said infectious diarrhea arises from a causative agent comprising at least one of bacteria, viruses, rotoviruses, retroviruses, parasites, fungi, protozoa, or toxins produced thereby.

5. The method according to claim 4 wherein said infectious diarrhea arises from bacteria and toxins produced thereby.

6. The method according to claim 5 wherein said infectious diarrhea arises from bacteria comprising at least one of Salmonella, Shigella, *V. Cholera*, Campylobacter, *Clostridium difficile*, *E. Coli*, *Trepomena hyodysemeriae*, or toxins produced thereby.

7. The method according to claim 6 wherein said infectious diarrhea arises from *Salmonella typhimurium*.

8. The method according to claim 6 wherein said infectious diarrhea arises from Shigella dysenteriae.

9. The method according to claim 6 wherein said infectious diarrhea arises from Cholera toxin.

10. The method according to claim 6 wherein the infectious diarrhea is caused by a strain of *V. Cholera* that does not produce cholera toxin.

11. The method according to claim 2 wherein the diarrhea arises as a side effect of at least one of cancer chemotherapeutic agents or radiation therapy.

12. The method according to claim 2 wherein the diarrhea arises from an inflammatory bowel disease comprising ulcerative colitis, Crohn's disease, or irritable bowel syndrome.

13. The method according to claim 2 wherein the diarrhea arises from an idiopathic condition.

14. The method according to claim 2 wherein the diarrhea arises as a side effect of ingestion of a food item.

15. The method according to claim 2 wherein the diarrhea arises in a mammal afflicted with a malabsorption condition.

16. The method according to claim 2 wherein the diarrhea arises as a side effect of a medicament other than a cancer chemotherapeutic agent, comprising at least one of an antibiotic, a broad spectrum antibacterial, an antifungal/ antibiotic, an interferon, a toxoid, a vaccine, a gastric antisecretory compound/proton pump inhibitor, a histamine $H_2$ antagonist, an antiemetic/antivertigo anticholinergic an antimigraine agent, an anti-gout agent, an antirheumatic agent, an antipsychotic agent, an antianxiety agent, an antidepressant, a nonsteroidal anti-inflammatory drug, a hyperlipidemic agent, an antihypertensive agent, a diuretic agent, a cardiac glycoside agent, an antianginal agent, an antiarrhythmic agent, a peripheral vasodilating agent, a β-adrenergic blocking agent, or an anorexiant.

17. The method according to claim 1 wherein said effective amount of at least one of D-histidine, L-histidine, a racemic mixture thereof, a non-racemic mixture thereof, or pharmaceutically acceptable salts thereof is between 1 mg/kg/day and 250 mg/kg/day.

18. The method according to claim 2 wherein said effective amount of at least one of D-histidine, L-histidine, a racemic mixture thereof, a non-racemic mixture thereof, or pharmaceutically acceptable salts thereof is between 1 mg/kg/day and 250 mg/kg/day.

19. The method according to claim 17 wherein said effective amount of at least one of D-histidine, L-histidine, a racemic mixture thereof, a non-racemic mixture thereof, or pharmaceutically acceptable salts thereof is administered by a route comprising oral, rectal, intraintestinal, intramuscular, intraperitoneal, intranasal, intravenous, implant and transdermal administration, or combinations thereof.

20. The method according to claim 18 wherein said effective amount of at least one of D-histidine, L-histidine, a racemic mixture thereof, a non-racemic mixture thereof, or pharmaceutically acceptable salts thereof is administered by a route comprising oral, rectal, intraintestinal, intramuscular, intraperitoneal, intranasal, intravenous, implant and transdermal administration, or combinations thereof.

21. The method according to claim 19 wherein said effective amount of at least one of D-histidine, L-histidine, a racemic mixture thereof, a non-racemic mixture thereof, or pharmaceutically acceptable salts thereof is administered in at least one of a timed-release, controlled-release, pulsed-release, sustained-release formulation or from a drug delivery device.

22. The method according to claim 20 wherein said effective amount of at least one of D-histidine, L-histidine, a racemic mixture thereof, a non-racemic mixture thereof or pharmaceutically acceptable salts thereof is administered in at least one of a timed-release, controlled-release, pulsed-release, sustained-release formulation or from a drug delivery device.

23. A method of preventing or reducing at least one of intestinal tract fluid secretions, fluid loss, or electrolyte loss in a mammal having diarrhea as a result of at least one of *Salmonella typhimurium* or Cholera toxin, by administering to at least one of peritoneum and intestinal lumen of said mammal a therapeutically effective amount of at least one of D-histidine, L-histidine, a racemic mixture thereof, a non-racemic mixture thereof, or pharmaceutically acceptable salts thereof.

24. The method according to claim 23 wherein a therapeutically effective amount of D-histidine or a pharmaceutically acceptable salt thereof is administered.

25. The method according to claim 23 wherein a therapeutically effective amount of D-histidine or a pharmaceutically acceptable salt thereof is administered.

26. A pharmaceutical composition for preventing or reducing at least one of extracellular fluid secretions, fluid loss, or electrolyte loss in a mammal undergoing or about to commence a therapeutic treatment, comprising a combination of a therapeutically effective amount of a medicament producing at least one of extracellular fluid secretions, fluid loss, and electrolyte loss as a side-effect, or a therapeutically effective amount of at least one of D-histidine, L-histidine, a racemic mixture thereof, a non-racemic mixture thereof, or pharmaceutically acceptable salts thereof, and a pharmaceutically inert carrier.

27. The pharmaceutical compostion according to claim 26 comprising a therapeutically effective dosage of ciprofloxacin, a therapeutically effective amount of at least one of D-histidine, L-histidine, a racemic mixture thereof, a non-racemic mixture thereof, and pharmaceutically acceptable salts thereof, or a pharmaceutically inert carrier.

28. The pharmaceutical compostion according to claim 26 comprising a therapeutically effective dosage of amoxicillin, a therapeutically effective amount of at least one of D-histidine, L-histidine, a racemic mixture thereof, a non-racemic mixture thereof, or pharmaceutically acceptable salts thereof, and a pharmaceutically inert carrier.

29. The pharmaceutical compostion according to claim 26 comprising a therapeutically effective dosage of cefuroxime axetil, a therapeutically effective amount of at least one of D-histidine, L-histidine, a racemic mixture thereof, a non-racemic mixture thereof, or pharmaceutically acceptable salts thereof, and a pharmaceutically inert carrier.

30. The pharmaceutical compostion according to claim 26 comprising a therapeutically effective dosage of erythromycin, a therapeutically effective amount of at least one of D-histidine, L-histidine, a racemic mixture thereof, a non-racemic mixture thereof, or pharmaceutically acceptable salts thereof, and a pharmaceutically inert carrier.

31. A pharmaceutical composition comprising a therapeutically effective amount of lactose-decomposing enzyme in combination with a therapeutically effective amount of at least one of D-histidine, L-histidine, a racemic mixture thereof, a non-racemic mixture thereof, or pharmaceutically acceptable salts thereof, and a pharmaceutically inert carrier.

32. The method according to claim 16, wherein said medicament is an antibiotic.

33. A method of preventing or treating post-antibiotic pseudomembranous colitis in a mammalian subject undergoing an antibiotic therapy, comprising administering to said subject a therapeutically effective amount of at least one of D-histidine, L-histidine, a racemic mixture thereof, a non-racemic mixture thereof, or pharmaceutically acceptable salts thereof, and a pharmaceutically inert carrier, for a period of time which is concurrent with and extends beyond said antibiotic therapy.

34. A method of preventing or reducing fluid/electrolyte loss and intestinal tissue damage associated with diarrhea in a mammal afflicted with ulcerative colitis, Crohn's disease, an irritable bowel syndrome, or an idiopathic diarrheal episode, by administering to said mammal an effective amount of at least one of D-histidine, L-histidine, a racemic mixture thereof, a non-racemic mixture thereof, or pharmaceutically acceptable salts thereof.

* * * * *